United States Patent
Davis

[11] Patent Number: 6,113,281
[45] Date of Patent: Sep. 5, 2000

[54] FIBEROPTIC CABLE APPARATUS WITH ADJUSTABLE FILTER

[76] Inventor: James M. Davis, 4687 Pond Apple Dr. South, Naples, Fla. 33999

[21] Appl. No.: 09/010,413

[22] Filed: Jan. 21, 1998

Related U.S. Application Data

[60] Provisional application No. 60/036,372, Jan. 22, 1997.

[51] Int. Cl.[7] .................................................. G02B 6/00
[52] U.S. Cl. .............................. 385/73; 385/901; 362/583
[58] Field of Search .............................. 385/901, 31, 73, 385/117, 119, 147; 362/583; 606/15–17

[56] References Cited

U.S. PATENT DOCUMENTS

| | | | |
|---|---|---|---|
| 3,195,405 | 7/1965 | Clark et al. | 88/61 |
| 5,426,474 | 6/1995 | Rubtsov et al. | 353/84 |
| 5,555,339 | 9/1996 | Migny et al. | 385/115 |
| 5,838,860 | 11/1998 | Kingstone et al. | 385/100 |

*Primary Examiner*—John D. Lee
*Assistant Examiner*—Victoria D. Hao
*Attorney, Agent, or Firm*—Willam E. Noonan

[57] ABSTRACT

A color adjustable light conducting apparatus is disclosed for use in combination with a standard fiberoptic illuminator having a light output port. The apparatus includes an elongate, light transmitting fiberoptic cable or other type of conductor. A fitting and a color adjuster is carried by a distal end of the cable. The color adjuster may include a filter wheel that is rotated to position a selected color filter in the cable. A fitting and a second color adjuster may be attached to a first end of the cable for interengaging the fiberoptic illuminator.

12 Claims, 2 Drawing Sheets

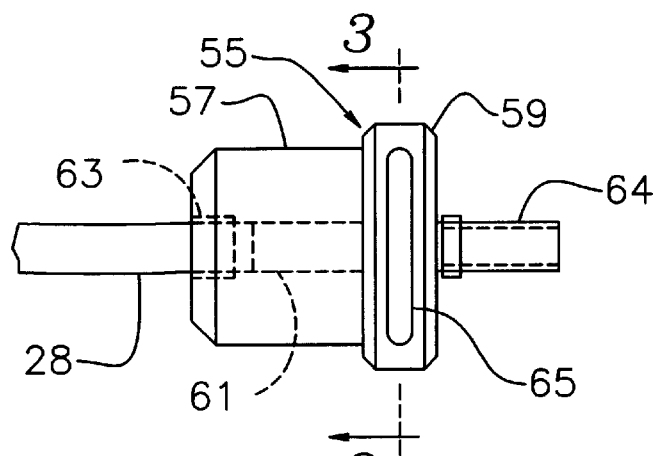
FIG. 2
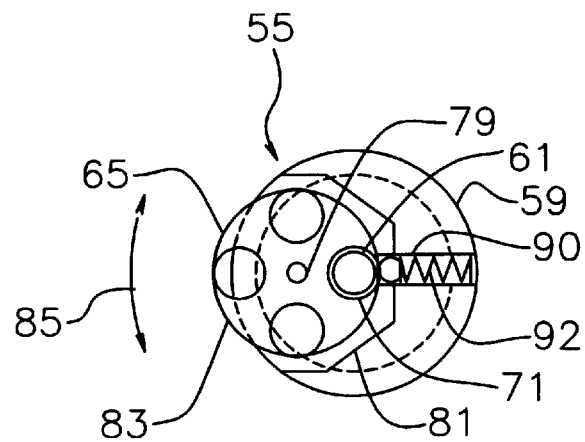
FIG. 3
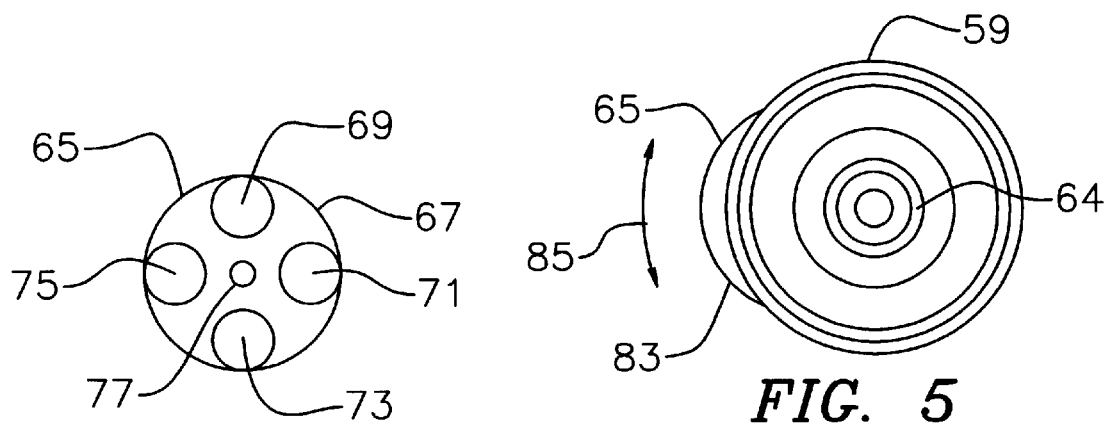
FIG. 4
FIG. 5

FIBEROPTIC CABLE APPARATUS WITH ADJUSTABLE FILTER

RELATED APPLICATION

This application is a continuation in part application of U.S. Provisional Patent Application Serial No. 60/036,372 filed Jan. 22, 1997.

FIELD OF THE INVENTION

This invention relates to a fiberoptic cable apparatus of the type used to illuminate medical procedures and, more particularly, to a fiberoptic cable or other light conductor that includes a rotatable filter wheel for adjusting the color of the light transmitted through the conductor.

BACKGROUND OF THE INVENTION

Fiberoptic illuminators are widely used to provide improved lighting for surgical and other medical procedures. Typically, the light generated by the illuminator is transmitted through a conventional fiberoptic cable to a head lamp, lens or other mechanism, which emits the light in a direction selected by the surgeon or other user of the device. Occasionally, the intensity and/or the color or wavelength of the emitted light requires adjustment. For example, the intensity may have to be selected to suit the particular setting or medical procedure that is involved and to provide adequate, but not blinding illumination of the object being illuminated. Different wavelengths or colors of light may be required to illuminate particular types of tissue, depending upon the medical procedure involved.

One serious limitation of conventional fiberoptic illuminators is that intensity and color adjustments must be made at the illuminator using standard knobs, dials, switches, digital touch pads and other forms of adjustment. Due to the typical distance between the illuminator and the patient being operated upon, adjusting the intensity or color has been a problem. The physician or surgeon usually must devote his or her full attention to the patient and to the particular surgical procedure being performed. As a result, an assistant is usually required to adjust the lighting at the illuminator. This can result in distractions to the doctor and/or miscommunications between the physician and the assistant.

An intensity adjustable fiberoptic cable apparatus is disclosed in my co-pending U.S. application Ser. No. 08/719,839, filed Sep. 30, 1996 (now U.S. Pat. No. 5,784,510). This product permits the physician to adjust the intensity of light through the fiberoptic cable by means of an adjustable iris located proximate either end of the cable. Although this apparatus provides for satisfactory intensity adjustments, it does not permit the color or wavelength of the light to be adjusted. To date, such color still must be selected through the use of a digital touch pad or other form of adjustment mounted on the fiberoptic illuminator housing.

SUMMARY OF INVENTION

It is therefore an object of this invention to provide a color adjustable apparatus that permits the color of light transmitted through and projected from a fiberoptic cable or other light conductor to be adjusted quickly, conveniently, accurately and personally by the surgeon or other person manipulating the light projecting instrument.

It is a further an object of this invention to provide an apparatus that accurately and adjustably filters the light emitted from a fiberoptic illuminator so that only a selected wavelength band is transmitted through an attached fiberoptic cable or other light conductor.

It is a further object of this invention to provide a color adjustable apparatus that permits the color of light from a fiberoptic illuminator to be adjusted without having to directly access the illuminator or manipulate dials, knobs or touch pads on the illuminator.

It is a further object of this invention to provide an apparatus that enables the color of light transmitted through a fiberoptic cable or other light conductor to be adjusted virtually instantaneously by the person using the cable without diverting that person's attention from the task at hand and without requiring the user to communicate color requirements to an assistant or other personnel.

It is a further an object of this invention to provide a color adjustable fiberoptic cable apparatus that reduces the number of persons required for certain medical procedures and surgical operations and which makes more efficient and better use of available medical personnel.

It is a further an object of this invention to provide a color adjustable fiberoptic cable apparatus that permits light color to be adjusted much more quickly and accurately than has heretofore been possible.

It is a further an object of this invention to provide a fiberoptic cable apparatus that permits precise wavelength bands of light to be selected to properly illuminate corresponding types of tissue.

It is a further an object of this invention to provide a fiberoptic cable apparatus having color adjusting mechanisms located at either end of the cable so that color adjustments may be achieved in a more flexible and versatile manner.

This invention results from a realization that the color or wavelength of illumination required for medical and surgical purposes may be adjusted quickly, accurately and efficiently by providing a filter wheel at the distal end of a light transmitting fiberoptic cable or other type of light conductor. This permits color adjustments to be made directly by a surgeon, doctor or other personnel manipulating the cable and pointing it at a patient or other object being illuminated. This means of color adjustment supplements and improves upon the conventional color adjustments located directly on the illuminator and significantly facilitates the use of fiberoptic illuminators in surgical and other medical operations. A similar filter wheel at the opposite, proximal end of the fiberoptic cable or light conductor allows an unfiltered illuminator to be retrofit for color adjustment.

This invention features a color adjustable light conducting apparatus for use in combination with a standard fiberoptic illuminator having a light source and a light output port. The apparatus includes means defining an elongate, light conductor such as a fiberoptic cable. There are means attached to a first end of the conductor for operably interengaging the output port of the fiberoptic illuminator and introducing light generated by the illuminator into the cable for transmission therethrough. Means are communicably connected to a distal, second end of the conductor for emitting transmitted light from the conductor. There are means attached to the conductor, between the means for interengaging and the means for emitting, for selectively adjusting the color or wavelength emitted from the conductor.

In a preferred embodiment, the means for adjusting may be interconnected between the second end of the conductor and the means for emitting. The means for adjusting may include an adjuster housing that is interconnected between the second end of the conductor and the means for emitting, and which has means defining an interior passageway through which light from the conductor is transmitted. The means for adjusting may further include a filter wheel mounted rotatably within the housing and carrying a plurality of light filters, each of which defines a selected wavelength or color band. The filter wheel is rotated to position a selected one of the filters across the passageway such that a selected color or wavelength band of light is transmitted through the passageway. The filter wheel is preferably mounted in an offset manner within the housing. The periphery of the filter wheel is engaged to rotate the wheel such that a selected filter is positioned in the passageway.

The means for adjusting may also include a means for adjusting the intensity of the light transmitted through the fiberoptic cable or other light conductor. Such means for adjusting the intensity are shown in my co-pending patent application Ser. No. 08/719,839 filed Sep. 30, 1996 (now U.S. Pat. No. 5,784,510). A fitting may be attached to the means for adjusting. The fitting may include a channel that conducts light from the means for adjusting and a discharge opening formed at the end of the channel. Light is emitted from the apparatus through the discharge opening. The fitting may comprise a fiberoptic plug that is selectively engageable with another, standard light projecting device.

DETAILED DESCRIPTION OF PREFERRED EMBODIMENTS

Other objects, features and advantages will occur from the following description of preferred embodiments and the accompanying drawings, in which:

FIG. 2 is an elevational side view of the color adjuster mechanism;

FIG. 3 is a cross sectional view of the color adjuster mechanism taken along line 3—3 of FIG. 2;

FIG. 4 is an elevational front view of the filter wheel; and

FIG. 5 is an elevational end view of the color adjuster mechanism.

Figure 1:
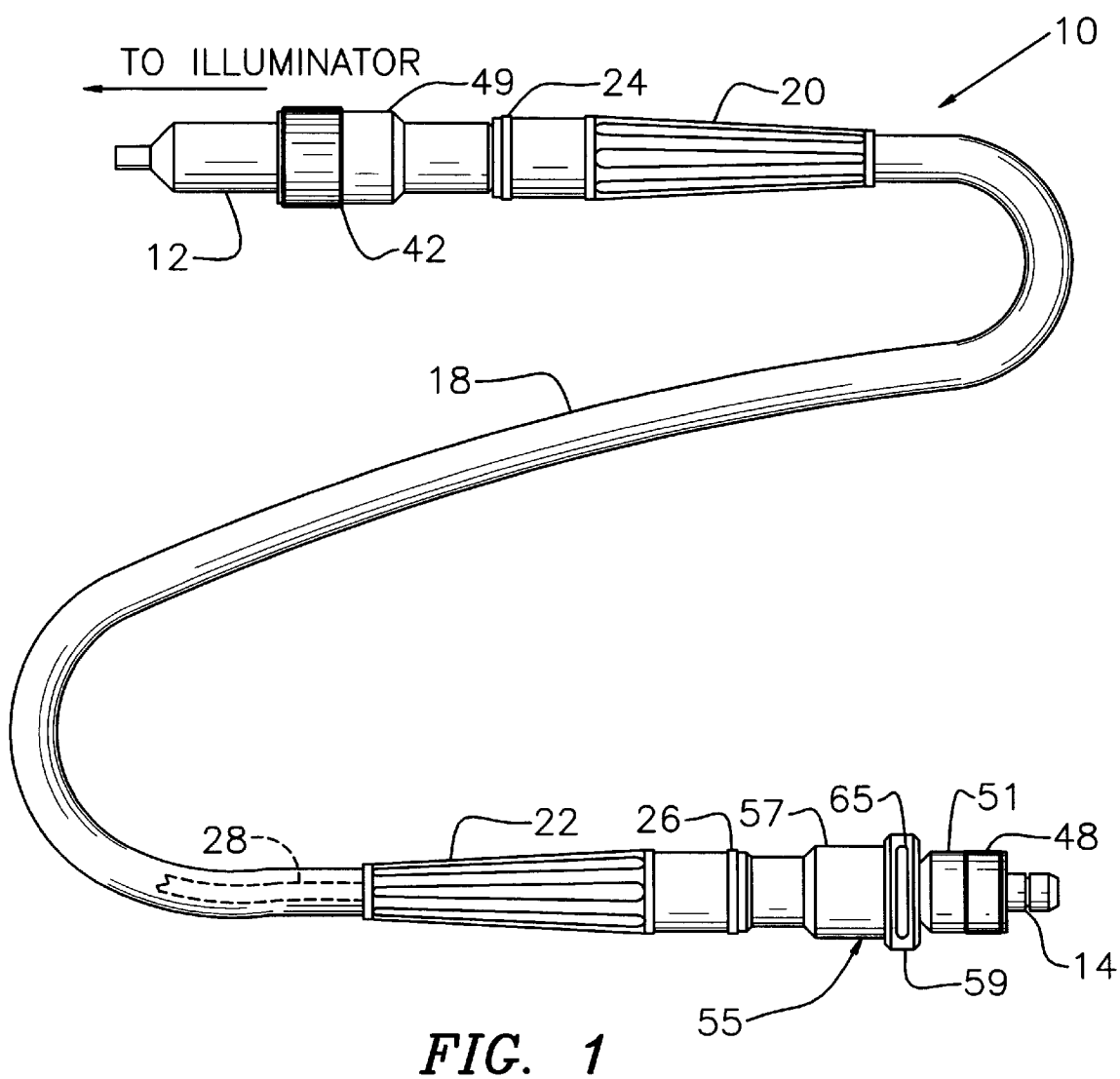
FIG. 1 is an elevational side view of a color adjustable fiberoptic cable apparatus according to this invention.

There is shown in FIG. 1 a color adjustable fiberoptic cable apparatus 10, which is selectively interengaged and used with a standard fiberoptic illuminator, not shown. Cable apparatus 10 may be utilized with a wide variety of conventional fiberoptic illuminators. Such illuminators are commonly used by the medical profession to provide lighting for surgery and other types of medical procedures. The illuminator does not comprise a part of this invention and is not specifically described herein. A typical illuminator includes various dials and gauges, as well as a standard light output port that is operably engaged by a plug or fitting 12 located at a first end of apparatus 10. The illuminator produces a desired type of light (e.g. halogen, neon, etc.) This light is introduced through the output port into fiberoptic cable apparatus 10 through plug 12. The light is then transmitted through apparatus 10 and emitted by standard end fitting 14 toward a body part or other object being illuminated. The fitting may also be engaged with a light projecting headlamp or analogous device. For the purpose of this invention, it is simply required that a standard illuminator having one or more light output ports be utilized. Such an illuminator is shown in my co-pending patent application Ser. No. 08/719,839 (now U.S. Pat. No. 5,784,510). An alternative arrangement of output ports is illustrated in the turret mechanism disclosed in U.S. patent application Ser. No. 08/384,927 filed Feb. 7, 1995 (now U.S. Pat. No. 5,617,302).

Apparatus 10 includes an elongate light conductor, namely a fiberoptic cable 18 that is operably interconnected between end fittings 12 and 14. Cable 18 typically comprises a conventional, universal fiberoptic cable having a construction that is well known to those skilled in the art. A tapered casing portion 20 is carried by cable 18 proximate a first end of cable apparatus 10 (the end closest to the illuminator) and a second tapered casing portion 22 is carried proximate the opposite, distal end of apparatus 10. A stepped cylindrical bushing 24 is attached to casing portion 20. A stepped cylindrical bushing 26 is similarly attached to casing portion 22. Fiberoptic cable 18 extends generally centrally through casing portions 20 and 22. Cable 18 carries an optical fiber conductor, not shown in FIG. 1 but see conductor 28 in FIG. 2. This is a standard single optical fiber or bundle of fibers, also shown and described in co-pending application Ser. No. 08/719,839 (now U.S. Pat. No. 5,784,510). The end of apparatus 10 proximate the illuminator includes an intensity adjuster mechanism 42. This mechanism is again described in co-pending patent application Ser. No. 08/719,839 (now U.S. Pat. No. 5,784,510) and such description is not repeated herein. It should be understood, nonetheless, that the optical fiber conductor 28 is operably interengaged with adjuster mechanism 42 in a manner described in that co-pending application. Similarly, a second adjustment mechanism 48 is formed proximate the opposite end of the cable apparatus. A fitting or bushing 49 is disposed between adjuster mechanism 42 and bushing 24. A similar bushing 51 is attached to adjuster mechanism 48.

A color adjuster mechanism 55, according to this invention, is interconnected between bushing 26 and bushing 51. Color adjuster mechanism 55, shown alone in FIGS. 2 and 3, includes a generally cylindrical housing 57 having a larger diameter flange 59 that is disposed adjacent to bushing 51. A central passageway 61 is formed axially through housing 57. A first end of passageway 61 includes a threaded receptacle 63. This receptacle communicably and threadably interengages with a complementary threaded end of optical fiber 28. An axial tubular element 64 is communicably joined to passageway 61 and extends from flanged end 59 of housing 57. Tubular element 64 extends centrally through bushing 51, FIG. 1, and communicably joins the central passageway formed through intensity adjuster mechanism 48.

A circular filter wheel 65, shown alone in FIG. 4, is rotatably mounted in flange portion 59 of adjuster housing 57. Filter wheel 65 includes a frame 67 and four individual light filters 69, 71, 73, and 75 that are mounted within frame 67. A central opening 77 is engaged by a pin 79, FIG. 3, that rotatably mounts wheel 65 within flange 59 of housing 57. As best shown in FIG. 3, the filter wheel is received in an octagonal recess 81 formed within flange 59. Wheel 65 is axially offset within housing 57 such that a selected one of the filters 69, 71, 73, and 75 may be positioned centrally in the cylindrical housing between passageway 61 and tubular element 63. This is accomplished by rotating wheel 65 about pin 79 to position the selected filter in front of passageway 61. As best shown in FIGS. 3 and 5, a peripheral portion 83 of wheel 65 protrudes from adjuster housing flange 59. As a result, the operator can place his or her thumb against peripheral edge 83 and rotate the filter wheel 65 in the directions indicated by double headed arrow 85. In this manner, a selected filter 69–75 may be operably positioned between passageway 61 and tubular element 64 so that only light of the corresponding color or wavelength band is transmitted through color adjuster mechanism 55.

The filter is held in place in the selected position by a locking dentent mechanism 90. This mechanism includes a spring loaded ball plunger 92 that is mounted within flange portion 59 of housing 57. A plurality of tiny recesses are formed about the circumference of wheel 65. Each recess is positioned proximate one of the filters 69, 71, 73, and 75. As the selected filter (filter 71 in FIG. 3) is rotated into position adjacent passageway 61, the ball of plunger 92 engages the recess to hold the filter wheel in that selected position. To manipulate the filter wheel into an alternative position, the operator simply presses his or her thumb against edge 83 of wheel 65 and rotates the wheel as indicated by double headed arrow 85. This urges the recess to disengage the ball of plunger 92. The plunger allows wheel 65 to rotate until the next selected filter is properly positioned in front of passageway 61. The recess associated with this filter then engages the ball plunger to provisionally lock the filter wheel and the selected filter in place within the adjuster housing.

By employing the above-described apparatus, color or wavelength bands transmitted through and emitted from cable 18 may be adjusted. Any desired number of filters may be employed in wheel 65. Typically, the filters and associated wavelength bands are selected to provide optimal illumination of various corresponding types of tissues. It should be understood that color adjuster mechanism 55 may also be located adjacent to plug 12 and intensity adjustment mechanism 42. In certain embodiments, a pair of color adjuster mechanisms 55 may be employed with each such mechanism located proximate a respective end of the fiberoptic cable apparatus. This permits the surgeon and/or an assistant to freely and conveniently adjust the color of light being transmitted. Interruptions and distractions are avoided.

In alternative embodiments, the above described fiberoptic cable may be replaced by a light conductor composed of a transparent light transmitting material. For example, the conductor may comprise a glass or transparent plastic rod or tube. In such embodiments, a color adjustment mechanism (and intensity controlling mechanisms) as described above, may be communicably attached at one or both ends of the light conductor. Alternatively, the color adjustment mechanism maybe inserted at some intermediate point along the light conductor. End fittings 12 and 14, as previously described, may be communicably attached to opposite ends of the light conductor by appropriate means of attachment.

It should be further understood that the color adjustment mechanism may be utilized with or without intensity adjustment mechanisms. One, two or no such intensity adjusters may be employed. Various forms of interconnecting the adjacent components on the fiberoptic cable apparatus may be utilized. Such constructions will be understood to those skilled in the art. Color adjuster mechanism 55 may be positioned along fiberoptic cable 18 at any convenient location, although it is preferred that it be placed proximate one or both of the ends of the cable. The particular means of interconnecting the color adjuster mechanism with other portions of the cable will be understood to those skilled in the art. A particularly preferred construction is illustrated in FIG. 2. In alternative embodiments, the filter wheel may employ other non-circular shapes.

Additional lengths of standard fiberoptic cable or other types of light conductors may be attached to the distal end of apparatus 10. This would be accomplished, for example, by simply plugging fitting 14 into another section of standard cable. In alternative embodiments, the light emitting fitting at the distal end of apparatus 10 may include threads or other means for interengaging a subsequent length of cable or conductor. In this manner, the light conductor may be constructed in any desired length and the color and intensity adjustment mechanisms may be located at desired positions that are convenient for the user.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. A color adjustable light conducting apparatus for use in combination with a standard fiberoptic illuminator having a light source and a light output port, said apparatus comprising:

means defining an elongate light conductor;

means attached to a first end of said conductor for operably interengaging the output port of the illuminator and introducing light generated by the illuminator into said conductor for transmission therethrough;

means communicably connected to a distal second end of said conductor for emitting light from said conductor; and means attached to said conductor, between said means for interengaging and said means for emitting, for selectively adjusting the color of light emitted from said conductor, said means for adjusting including an adjuster housing connected to said conductor, said adjuster housing having an interior passageway communicably engaged with said conductor and through which light is transmitted, said passageway having opposing first and second ends, said means for adjusting further including a filter wheel mounted rotatably within said housing and extending across said passageway between said first and second ends thereof, said filter wheel carrying a plurality of light filters, each said filter transmitting a selected wavelength band, said wheel being rotated to position a selected filter across said passageway between said first and second ends thereof such that a corresponding wavelength band of light is transmitted through said passageway, said filter wheel being mounted within said housing such that a peripheral portion of said wheel is exposed from said housing, said peripheral portion being manually engaged to rotate said filter wheel and position a selected filter across said passageway.

2. The apparatus of claim 1 in which said light conductor includes a fiberoptic cable.

3. The apparatus of claim 1 in which said adjuster housing is interconnected between said second end of said conductor and said means for emitting.

4. The apparatus of claim 1 further including means attached to said conductor between said means for interengaging and said means for emitting for controlling the intensity of light transmitted though said conductor.

5. The apparatus of claim 1 in which said means for adjusting interconnects said second end of said conductor and said means for emitting.

6. The apparatus of claim 1 in which said means for emitting includes a fitting connected to said means for adjusting and having a channel formed therethrough, said channel being communicable with said passageway, said fitting further including a discharge opening formed at a distal end of said channel for discharging light therethrough.

7. The apparatus of claim 6 in which said fitting comprises a plug that is selectively engaged with a standard light projecting device.

8. The apparatus of claim 1 in which said adjuster housing has a generally cylindrical shape.

9. A color adjustable light conducting apparatus for use in combination with a standard fiberoptic illuminator having a light source and a light output port, said apparatus comprising:

means defining an elongate light conductor;

means attached to a first end of said conductor for operably interengaging the output port of the illuminator and introducing light generated by the illuminator into said conductor for transmission therethrough;

means communicably connected to a distal second end of said conductor for emitting light from said conductor; and means attached to said conductor, between said means for interengaging and said means for emitting, for selectively adjusting the color of light emitted from said conductor, said means for adjusting including an adjuster housing connected to said conductor, said adjuster housing having an interior passageway communicably engaged with said conductor and through which light is transmitted, said passageway having opposing first and second ends, said means for adjusting further including a filter wheel mounted rotatably within said housing and extending across said passageway between said first and second ends thereof, said filter wheel carrying a plurality of light filters, each said filter transmitting a selected wavelength band, said wheel being rotated to position a selected filter across said passageway between said first and second ends thereof such that a corresponding wavelength band of light is transmitted through said passageway, said filter wheel being mounted within said housing such that a peripheral portion of said wheel is exposed from said housing, said peripheral portion being manually engaged to rotate said filter wheel and position a selected filter across said passageway;

said means for emitting including a fitting connected to said adjuster housing and having a channel formed therethrough, said channel being communicably engaged with said passageway, said fitting further including a discharge opening formed at a distal end of said channel for discharging light therefrom.

10. The apparatus of claim 9 in which said fitting comprises a plug that is selectively engaged with a standard light projecting device.

11. A color adjustable light conducting apparatus for use in combination with a standard fiberoptic illuminator having a light source and a light output port, said apparatus comprising:

means defining an elongate light conductor;

means attached to a first end of said conductor for operably interengaging the output port of the illuminator and introducing light generated by the illuminator into said conductor for transmission therethrough;

means communicably connected to a distal second end of said conductor for emitting light from said conductor; and means attached to said conductor, between said means for interengaging and said means for emitting, for selectively adjusting the color of light emitted from said conductor, said means for adjusting including a generally cylindrical adjuster housing having an elongate interior passageway communicably engaged with said conductor and through which light is transmitted, said passageway having opposing first and second ends, said means for adjusting further including a filter wheel mounted rotatably within said housing and extending across said passageway between said first and second ends thereof, said filter wheel carrying a plurality of light filters, each said filter transmitting a selected wavelength band, said wheel being rotated to position a selected filter across said passageway between said first and second ends thereof such that a corresponding wavelength band of light is transmitted through said passageway, said filter wheel being mounted within said housing such that a peripheral portion of said wheel is exposed from said housing, said peripheral portion being manually engaged to rotate said filter wheel and position a selected filter across said passageway;

said means for emitting including a fitting connected to said adjuster housing and having a channel formed therethrough, said channel being communicably engaged with said passageway, said fitting further including a discharge opening formed at a distal end of said channel for discharging light therefrom;

said second end of said conductor being directly connected to said first end of said passageway and said fitting being directly engaged with said second end of said passageway such that said filter wheel extends across said passageway between said second end of said conductor and said filter.

12. The apparatus of claim 11 in which said filter wheel is centrally offset within said housing.

* * * * *